(12) United States Patent
McCabe (10) Patent No.: US 7,770,712 B2
(45) Date of Patent: Aug. 10, 2010

(54) ARTICLE TRANSFER AND PLACEMENT APPARATUS WITH ACTIVE PUCK

(75) Inventor: John A. McCabe, Sheboygan Falls, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 345 days.

(21) Appl. No.: 11/357,546

(22) Filed: Feb. 17, 2006

(65) Prior Publication Data

US 2007/0193856 A1    Aug. 23, 2007

(51) Int. Cl.
- B65G 15/44 (2006.01)
- B65G 13/02 (2006.01)
- B65G 17/46 (2006.01)
- B65G 47/00 (2006.01)
- B65G 37/00 (2006.01)
- B65G 47/82 (2006.01)

(52) U.S. Cl. ............... 198/463.1; 198/698; 198/699.1; 198/471.1; 198/478.1; 198/598

(58) Field of Classification Search ............ 198/688.1, 198/689.1, 471.1, 478.1, 598
See application file for complete search history.

(56) References Cited

U.S. PATENT DOCUMENTS

| | | | |
|---|---|---|---|
| 135,145 A | 1/1873 | Murphy | |
| 293,353 A | 2/1884 | Purvis | |
| 312,257 A | 2/1885 | Cotton et al. | |
| 410,123 A | 8/1889 | Stilwell | |
| 432,742 A | 7/1890 | Stanley | |
| 643,821 A | 2/1900 | Howlett | |
| 1,393,524 A | 10/1921 | Grupe | |
| 1,605,842 A | 11/1926 | Jones | |
| 1,686,595 A | 10/1928 | Belluche | |
| 1,957,651 A | 5/1934 | Joa | |
| 2,009,857 A | 7/1935 | Potdevin | |
| 2,054,832 A | 9/1936 | Potdevin | |
| 2,117,432 A | 5/1938 | Linscott | |
| 2,128,746 A | 8/1938 | Joa | |
| 2,131,808 A | 10/1938 | Joa | |
| 2,164,408 A | 7/1939 | Joa | |
| 2,167,179 A | 7/1939 | Joa | |
| 2,171,741 A | 9/1939 | Cohn et al. | |
| 2,213,431 A | 9/1940 | Joa | |
| 2,254,290 A | 9/1941 | Joa | |
| 2,254,291 A | 9/1941 | Joa | |

(Continued)

FOREIGN PATENT DOCUMENTS

BE    1007854    11/1995

(Continued)

OTHER PUBLICATIONS

Reciprocating Mechanisms, Ingenious Mechanisms for Designers and Inventors, Franklin Jones vol. 1.

*Primary Examiner*—Gene Crawford
*Assistant Examiner*—Yolanda Cumbess
(74) *Attorney, Agent, or Firm*—Ryan Kromholz & Manion, S.C (57) ABSTRACT

An apparatus for transferring articles such as absorbent cores or disposable diaper chassis components from a rotary mechanism, such as a pad turner, to a linear mechanism, such as a conveyor, for further processing. A puck on the apparatus is capable of manipulating the article during this transfer procedure.

3 Claims, 7 Drawing Sheets

U.S. PATENT DOCUMENTS

| | | |
|---|---|---|
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,811,905 A | 11/1957 | Kennedy, Jr. |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,913,862 A | 11/1959 | Sabee |
| 2,939,461 A | 6/1960 | Joa |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller, Jr. |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,607,578 A | 9/1971 | Olof Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerle |
| 3,772,120 A | 11/1973 | Radzins |
| 3,796,360 A | 3/1974 | Alexeff |
| 3,816,210 A | 6/1974 | Aoka et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisnecki et al. |
| 4,672,705 A | 6/1987 | Bors et al. |
| 4,675,062 A | 6/1987 | Instance |
| 4,693,056 A | 9/1987 | Raszewski |

| | | | | | | |
|---|---|---|---|---|---|---|
| 4,701,239 A | 10/1987 | Craig | | 5,531,850 A | 7/1996 | Herrmann |
| 4,726,874 A | 2/1988 | VanVliet | | 5,540,647 A | 7/1996 | Weiermann et al. |
| 4,726,876 A | 2/1988 | Tomsovic et al. | | 5,545,275 A | 8/1996 | Herrin et al. |
| 4,743,241 A | 5/1988 | Igaue et al. | | 5,545,285 A | 8/1996 | Johnson |
| 4,751,997 A | 6/1988 | Hirsch | | 5,552,013 A | 9/1996 | Ehlert et al. |
| 4,753,429 A | 6/1988 | Irvine et al. | | 5,556,360 A | 9/1996 | Kober et al. |
| 4,756,141 A | 7/1988 | Hirsch et al. | | 5,556,504 A | 9/1996 | Rajala et al. |
| 4,764,325 A | 8/1988 | Angstadt | | 5,560,793 A | 10/1996 | Ruscher et al. |
| 4,765,780 A | 8/1988 | Angstadt | | 5,602,747 A | 2/1997 | Rajala |
| 4,776,920 A | 10/1988 | Ryan | | 5,624,420 A | 4/1997 | Bridges et al. |
| 4,777,513 A | 10/1988 | Nelson | | 5,624,428 A | 4/1997 | Sauer |
| 4,782,647 A | 11/1988 | Williams et al. | | 5,628,738 A | 5/1997 | Suekane |
| 4,785,986 A | 11/1988 | Daane et al. | | 5,634,917 A | 6/1997 | Fujioka et al. |
| 4,795,510 A | 1/1989 | Wittrock et al. | | 5,643,165 A | 7/1997 | Klekamp |
| 4,801,345 A | 1/1989 | Dussaud et al. | | 5,643,396 A | 7/1997 | Rajala et al. |
| 4,802,570 A | 2/1989 | Hirsch et al. | | 5,645,543 A | 7/1997 | Nomura et al. |
| 4,840,609 A | 6/1989 | Jones et al. | | 5,659,229 A | 8/1997 | Rajala |
| 4,845,964 A | 7/1989 | Bors et al. | | 5,660,657 A | 8/1997 | Rajala et al. |
| 4,864,802 A | 9/1989 | D'Angelo | | 5,660,665 A * | 8/1997 | Jalonen ................... 156/163 |
| 4,880,102 A | 11/1989 | Indrebo | | 5,683,376 A | 11/1997 | Kato et al. |
| 4,888,231 A | 12/1989 | Angstadt | | RE35,687 E | 12/1997 | Igaue et al. |
| 4,892,536 A | 1/1990 | Des Marais et al. | | 5,693,165 A | 12/1997 | Schmitz |
| 4,904,440 A | 2/1990 | Angstadt | | 5,699,653 A | 12/1997 | Hartman et al. |
| 4,908,175 A | 3/1990 | Angstadt | | 5,707,470 A | 1/1998 | Rajala et al. |
| 4,909,019 A | 3/1990 | Delacretaz et al. | | 5,711,832 A | 1/1998 | Glaug et al. |
| 4,925,520 A | 5/1990 | Beaudoin et al. | | 5,725,518 A | 3/1998 | Coates |
| 4,927,322 A | 5/1990 | Schweizer et al. | | 5,745,922 A | 5/1998 | Rajala et al. |
| 4,927,582 A | 5/1990 | Bryson | | 5,746,869 A | 5/1998 | Hayden et al. |
| 4,937,887 A | 7/1990 | Schreiner | | 5,749,989 A | 5/1998 | Linman et al. |
| 4,963,072 A | 10/1990 | Miley et al. | | 5,788,797 A | 8/1998 | Herrin et al. |
| 4,987,940 A | 1/1991 | Straub et al. | | 5,817,199 A | 10/1998 | Brennecke et al. |
| 4,994,010 A | 2/1991 | Doderer-Winkler | | 5,829,164 A | 11/1998 | Kotitschke |
| 5,000,806 A | 3/1991 | Merkatoris et al. | | 5,836,931 A | 11/1998 | Toyoda et al. |
| 5,021,111 A | 6/1991 | Swenson | | 5,858,012 A | 1/1999 | Yamaki et al. |
| 5,025,910 A | 6/1991 | Lasure et al. | | 5,865,393 A | 2/1999 | Kreft et al. |
| 5,045,039 A | 9/1991 | Bay | | 5,868,727 A | 2/1999 | Barr et al. |
| 5,062,597 A | 11/1991 | Martin et al. | | 5,876,027 A | 3/1999 | Fukui et al. |
| 5,064,179 A | 11/1991 | Martin et al. | | 5,876,792 A | 3/1999 | Caldwell |
| 5,080,741 A | 1/1992 | Nomura et al. | | 5,879,500 A | 3/1999 | Herrin et al. |
| 5,094,658 A | 3/1992 | Smithe et al. | | 5,902,431 A | 5/1999 | Wilkinson et al. |
| 5,096,532 A | 3/1992 | Neuwirth et al. | | 5,932,039 A | 8/1999 | Popp et al. |
| 5,108,017 A | 4/1992 | Adamski et al. | | 5,938,193 A | 8/1999 | Bluemle et al. |
| 5,109,767 A | 5/1992 | Nyfeler et al. | | 5,964,970 A | 10/1999 | Woolwine et al. |
| 5,110,403 A | 5/1992 | Ehlert | | 6,036,805 A | 3/2000 | McNichols |
| 5,127,981 A | 7/1992 | Straub et al. | | 6,043,836 A | 3/2000 | Kerr et al. |
| 5,131,525 A | 7/1992 | Musschoot | | 6,050,517 A | 4/2000 | Dobrescu et al. |
| 5,147,487 A | 9/1992 | Nomura et al. | | 6,074,110 A | 6/2000 | Verlinden et al. |
| 5,163,594 A | 11/1992 | Meyer | | 6,076,442 A | 6/2000 | Arterburn et al. |
| 5,171,239 A | 12/1992 | Igaue et al. | | 6,098,249 A | 8/2000 | Toney et al. |
| 5,176,244 A | 1/1993 | Radzins et al. | | 6,123,792 A | 9/2000 | Samida et al. |
| 5,183,252 A | 2/1993 | Wolber et al. | | 6,171,432 B1 | 1/2001 | Brisebois et al. |
| 5,188,627 A | 2/1993 | Igaue et al. | | 6,183,576 B1 | 2/2001 | Couillard et al. |
| 5,195,684 A | 3/1993 | Radzins | | 6,210,386 B1 | 4/2001 | Inoue |
| 5,203,043 A | 4/1993 | Riedel | | 6,212,859 B1 | 4/2001 | Bielik, Jr. et al. |
| 5,213,645 A | 5/1993 | Nomura et al. | | 6,250,048 B1 | 6/2001 | Linkiewicz |
| 5,226,992 A | 7/1993 | Morman | | 6,264,784 B1 | 7/2001 | Menard et al. |
| 5,246,433 A | 9/1993 | Hasse et al. | | 6,276,421 B1 | 8/2001 | Valenti et al. |
| 5,267,933 A | 12/1993 | Precoma | | 6,306,122 B1 | 10/2001 | Narawa et al. |
| 5,308,345 A | 5/1994 | Herrin | | 6,309,336 B1 | 10/2001 | Muessig et al. |
| 5,328,438 A | 7/1994 | Crowley | | 6,312,420 B1 | 11/2001 | Sasaki et al. |
| 5,340,424 A | 8/1994 | Matsushita | | 6,314,333 B1 | 11/2001 | Rajala et al. |
| 5,368,893 A | 11/1994 | Sommer et al. | | 6,315,022 B1 | 11/2001 | Herrin et al. |
| 5,407,507 A * | 4/1995 | Ball ........................ 156/163 | | 6,336,921 B1 | 1/2002 | Kato et al. |
| 5,407,513 A | 4/1995 | Hayden et al. | | 6,358,350 B1 | 3/2002 | Glaug et al. |
| 5,415,649 A | 5/1995 | Watanabe et al. | | 6,369,291 B1 | 4/2002 | Uchimoto et al. |
| 5,421,924 A | 6/1995 | Ziegelhoffer et al. | | 6,375,769 B1 | 4/2002 | Quereshi et al. |
| 5,424,025 A | 6/1995 | Hanschen et al. | | 6,391,013 B1 | 5/2002 | Suzuki et al. |
| 5,429,576 A | 7/1995 | Doderer-Winkler | | 6,416,697 B1 | 7/2002 | Venturino et al. |
| 5,435,802 A | 7/1995 | Kober | | 6,443,389 B1 | 9/2002 | Palone |
| 5,449,353 A | 9/1995 | Watanabe et al. | | 6,446,795 B1 | 9/2002 | Allen et al. |
| 5,464,401 A | 11/1995 | Hasse et al. | | 6,473,669 B2 | 10/2002 | Rajala et al. |
| 5,486,253 A | 1/1996 | Otruba | | 6,475,325 B1 | 11/2002 | Parrish et al. |
| 5,494,622 A | 2/1996 | Heath et al. | | 6,478,786 B1 | 11/2002 | Gloug et al. |

| | | | | | |
|---|---|---|---|---|---|
| 6,482,278 | B1 | 11/2002 | McCabe et al. | CA | 1153345 | 9/1983 |
| 6,494,244 | B2 | 12/2002 | Parrish et al. | CA | 1190078 | 7/1985 |
| 6,521,320 | B2 | 2/2003 | McCabe et al. | CA | 1210744 | 9/1986 |
| 6,524,423 | B1 | 2/2003 | Hilt et al. | CA | 1212132 | 9/1986 |
| 6,551,228 | B1 | 4/2003 | Richards | CA | 1236056 | 5/1988 |
| 6,551,430 | B1 | 4/2003 | Glaug et al. | CA | 1249102 | 1/1989 |
| 6,554,815 | B1 | 4/2003 | Umebayashi | CA | 1292201 | 11/1991 |
| 6,572,520 | B2 | 6/2003 | Blumle | CA | 1307244 | 9/1992 |
| 6,581,517 | B1 | 6/2003 | Becker et al. | CA | 1308015 | 9/1992 |
| 6,596,108 | B2 | 7/2003 | McCabe | CA | 1310342 | 11/1992 |
| 6,605,172 | B1 | 8/2003 | Anderson et al. | CA | 2023816 | 3/1994 |
| 6,605,173 | B2 | 8/2003 | Glaug et al. | CA | 2404154 | 10/2001 |
| 6,637,583 | B1 | 10/2003 | Andersson | CA | 2541194 | 1/2006 |
| 6,648,122 | B1 | 11/2003 | Hirsch et al. | CA | 2559517 | 5/2007 |
| 6,649,010 | B2 | 11/2003 | Parrish et al. | DE | 102006047280 | 4/2007 |
| 6,659,150 | B1 | 12/2003 | Perkins et al. | EP | 0044206 | 1/1982 |
| 6,659,991 | B2 | 12/2003 | Suckane | EP | 0048011 | 3/1982 |
| 6,675,552 | B2 | 1/2004 | Kunz et al. | EP | 0089106 | 9/1983 |
| 6,684,925 | B2 | 2/2004 | Nagate et al. | EP | 0304140 | 8/1987 |
| 6,743,324 | B2 | 6/2004 | Hargett et al. | EP | 0439897 | 2/1990 |
| 6,766,817 | B2 | 7/2004 | da Silva | EP | 0455231 | 11/1991 |
| D497,991 | S | 11/2004 | Otsubo et al. | EP | 510251 | 10/1992 |
| 6,820,671 | B2 | 11/2004 | Calvert | EP | 0652175 | 5/1995 |
| 6,837,840 | B2 | 1/2005 | Yonekawa et al. | EP | 0811473 | 12/1997 |
| 6,840,616 | B2 | 1/2005 | Summers | EP | 0901780 | 3/1999 |
| 6,852,186 | B1 | 2/2005 | Matsuda et al. | EP | 990588 | 4/2000 |
| 6,875,202 | B2 | 4/2005 | Kumasaka et al. | EP | 1132325 | 9/2001 |
| 6,893,528 | B2 | 5/2005 | Middelstadt et al. | EP | 1272347 | 1/2003 |
| 6,918,404 | B2 | 7/2005 | Dias da Silva | EP | 1571249 | 9/2005 |
| 6,978,486 | B2 | 12/2005 | Zhou et al. | EP | 1619008 | 1/2006 |
| 7,066,586 | B2 | 6/2006 | da Silva | EP | 1707168 | 4/2006 |
| 7,077,393 | B2 | 7/2006 | Ishida | ES | 509706 | 11/1982 |
| 7,172,666 | B2 | 2/2007 | Groves et al. | ES | 520559 | 12/1983 |
| 7,214,174 | B2 | 5/2007 | Allen et al. | ES | 296211 | 12/1987 |
| 7,247,219 | B2 | 7/2007 | O'Dowd | FR | 2255961 | 7/1975 |
| 2001/0012813 | A1 | 8/2001 | Bluemle | FR | 0206208 | 12/1986 |
| 2001/0017181 | A1 | 8/2001 | Otruba et al. | FR | 2891811 | 4/2007 |
| 2002/0046802 | A1 | 4/2002 | Tachibana et al. | GB | 191101501 | 1/1912 |
| 2002/0059013 | A1 | 5/2002 | Rajala et al. | GB | 439897 | 12/1935 |
| 2003/0000620 | A1 | 1/2003 | Herrin et al. | GB | 856389 | 12/1960 |
| 2003/0015209 | A1 | 1/2003 | Gingras et al. | GB | 941073 | 11/1963 |
| 2003/0052148 | A1 | 3/2003 | Rajala et al. | GB | 1096373 | 12/1967 |
| 2003/0066585 | A1 | 4/2003 | McCabe | GB | 1126539 | 9/1968 |
| 2003/0083638 | A1 | 5/2003 | Malee | GB | 1346329 | 2/1974 |
| 2003/0084984 | A1 | 5/2003 | Glaug et al. | GB | 1412812 | 11/1975 |
| 2003/0089447 | A1 | 5/2003 | Molee et al. | GB | 2045298 | 10/1980 |
| 2003/0135189 | A1 | 7/2003 | Umebayashi | GB | 2288316 | 10/1995 |
| 2004/0007328 | A1 | 1/2004 | Popp et al. | JP | 428364 | 1/1992 |
| 2004/0016500 | A1 | 1/2004 | Tachibana et al. | JP | 542180 | 2/1993 |
| 2004/0112517 | A1 | 6/2004 | Groves et al. | JP | 576566 | 3/1993 |
| 2004/0164482 | A1 | 8/2004 | Edinger | JP | 626160 | 2/1994 |
| 2005/0000628 | A1 | 1/2005 | Norrley | JP | 626161 | 2/1994 |
| 2005/0196538 | A1 | 9/2005 | Sommer et al. | JP | 6197925 | 7/1994 |
| 2005/0230056 | A1 | 10/2005 | Meyer et al. | JP | 10035621 | 2/1998 |
| 2005/0230449 | A1 | 10/2005 | Meyer et al. | JP | 10-277091 | 10/1998 |
| 2005/0233881 | A1 | 10/2005 | Meyer | SE | 0602047 | 5/2007 |
| 2005/0234412 | A1 | 10/2005 | Andrews et al. | WO | WO9747265 | 12/1997 |
| 2005/0257881 | A1 | 11/2005 | Coose et al. | WO | WO 9747810 | 12/1997 |
| 2005/0275148 | A1 | 12/2005 | Beaudoin et al. | WO | WO9907319 | 2/1999 |
| 2006/0021300 | A1 | 2/2006 | Tada et al. | WO | WO9913813 | 3/1999 |
| 2006/0137298 | A1 | 6/2006 | Oshita et al. | WO | WO9965437 | 12/1999 |
| 2006/0224137 | A1 | 10/2006 | McCabe et al. | WO | WO0143682 | 6/2001 |
| 2006/0265867 | A1 | 11/2006 | Schaap | WO | WO0172237 | 10/2001 |
| 2007/0074953 | A1 | 4/2007 | McCabe | WO | WO2005075163 | 1/2005 |

FOREIGN PATENT DOCUMENTS

| | | | |
|---|---|---|---|
| CA | 1146129 | 5/1983 | |

* cited by examiner

ARTICLE TRANSFER AND PLACEMENT APPARATUS WITH ACTIVE PUCK

BACKGROUND OF THE INVENTION

This invention related to an apparatus for transferring articles such as absorbent pads in the manufacture of disposable absorbent articles such as diapers, incontinence control garments or female sanitary pads as they advance along a production line.

In the production and manufacture of disposable products such as sanitary napkins-or pants-type diapers, it frequently becomes necessary to manufacture a component of the product in one orientation, and then to rotate that component part 90° so that it is suitably oriented for use in another step in the production process. Various devices have been developed for this purpose and are known to those experienced in the industry. Examples of such apparatus are those described in U.S. Pat. Nos. 4,726,876, 4,880,102, and 5,025,910, the disclosures of which are incorporated herein by reference.

As discussed above, a typical article to be reoriented by the apparatus of this invention is an absorbent pad. Because absorbent pads are typically comprised of several webs, an absorbent core and several elastic members, there is a tendency of these assemblies to contract and become distorted during transfer operations which greatly complicates handling of the pad during further processing. Control of the pad is important.

SUMMARY OF THE INVENTION

The apparatus of the present invention is an active puck that is capable of rotating and stretching an article between a pick-up and a lay-down point.

An active puck is disclosed that picks up an article from a first conveying means, the article traveling in a first orientation, carries, stretches and rotates the article, so the article is traveling in a second orientation, and deposits the article onto another conveying means. A cam plate comprising a guiding structure of increasing radius cooperates with a vacuum slide to urge stretching of the article is provided. A vacuum puck carries the article while the slide rotatably operates through the increasing (or decreasing) radius.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
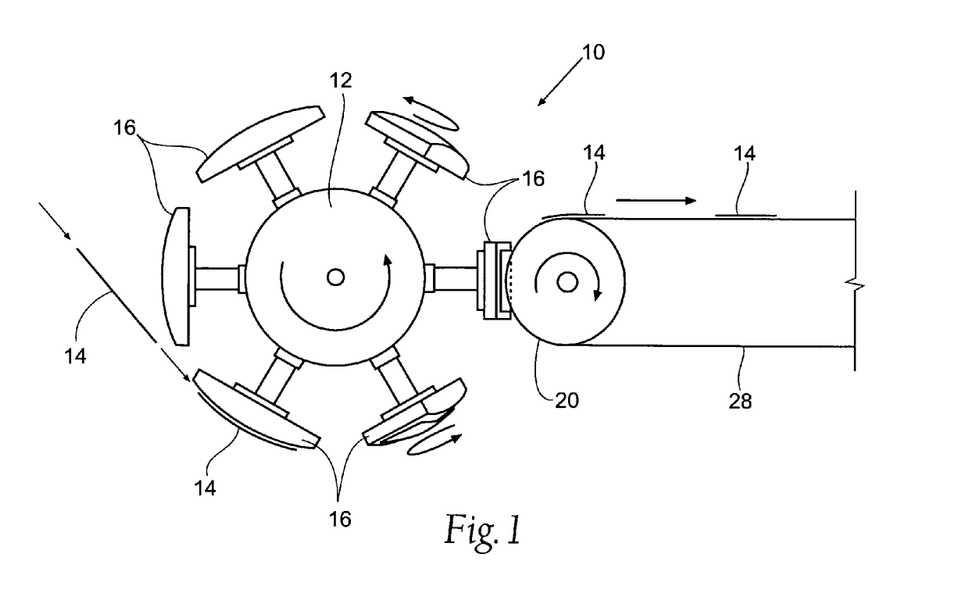
FIG. 1 is a fragmentary side elevation view, shown in diagrammatic form, of a pad transferring assembly.

Referring more particularly to the drawings, there is seen in FIG. 1 an apparatus 10 carrying pucks, or transfer heads 16, of the present invention. The apparatus 10 is adapted to receive a series of articles 14 from an upstream conveyor or vacuum drum (not shown) onto a pad turning device 12 which includes a plurality of radially extending transfer heads 16.

The location where articles 14 are received from the upstream point onto the pucks 16 is known as the pick up point. The location where articles 14 are deposited from the pucks 16 to a downstream drum or conveyor 20 is known as the lay down point.

The pad turning device 12 may be, for example, a rotary pad turner of the type more fully described in U.S. Pat. No. 5,025,910 which is incorporated herein by reference. The articles 14, such as absorbent pads, may be any elongated articles which need to be rotated approximately 90° during the course of a manufacturing operation. In the present invention, the elongated articles are also stretched away from their center point in a direction, such as a radial direction, away from the axis of the puck 16 as will be described later.

Such pad turning devices 12 are especially needed and are suited for use in connection with the manufacture and packaging of sanitary napkins as well as absorbent pads which are used in the assembly of disposable garments such as adult incontinence garments or children's training pants.

Also seen in FIG. 1, articles 14 are successively and individually picked-up by the transfer heads 16 of the pad transfer device 12. In the illustrated embodiment, the articles 14 are picked up from a vacuum drum (not shown). Various conventional conveying and direction changing devices such as rollers may be employed in the feeding of the web and do not form a part of this invention.

After the articles 14 have been rotated 90 degrees, they are deposited at the lay down point onto drum 20. The pucks 16 of the present invention can stretch the articles 14, as will be described below, and deposit them in the stretched condition onto drum 20. A conveyor 28 or the like transport the articles 14 for further processing or to a packaging device, as required by a particular application.

Figure 2:
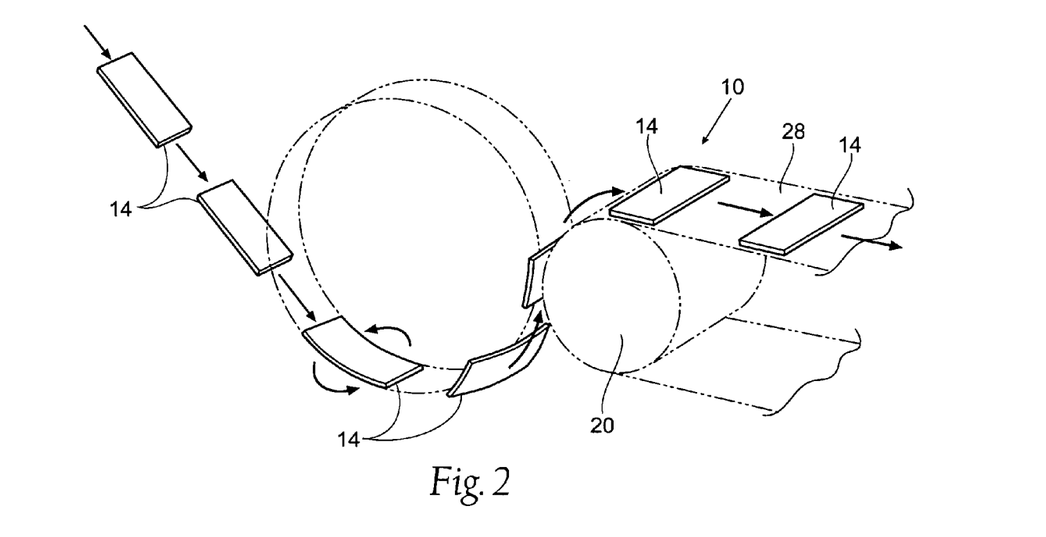
FIG. 2 is a perspective fragmentary, diagrammatic view, showing related apparatus by means of phantom lines and illustrating the path of movement of pads moving in accordance with the invention.

Referring to FIG. 2, there is seen a diagrammatic depiction of the travel path of the web 22 and the resultant pads 14 which are formed therefrom. In this depiction the various apparatus have been eliminated but are partially illustrated by means of phantom lines.

Figure 3:
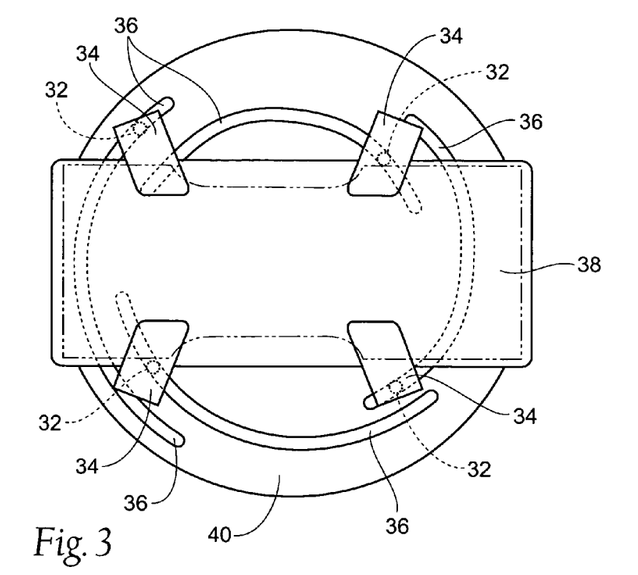
FIG. 3 is a top view of an embodiment of an active pad turning puck of the present invention.
Figure 4:
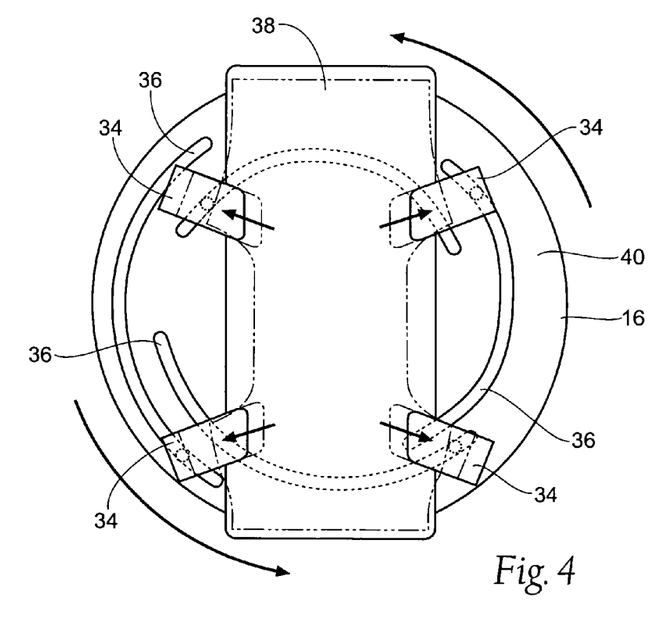
FIG. 4 is a top view of an embodiment of an active pad turning puck of the present invention.

As can be seen, the article is rotated 90° from the pick up point to the lay down point, and is also stretched during this time it spends on the puck 16. The active puck 16 of this invention is more fully described in the remaining Figures. Referring generally to FIGS. 2, 3 and 4, the process of constructing disposable products is traditionally performed in assembly-line fashion, with the product construction generally following a "machine direction." The machine direction is understood, in reference to FIG. 2, to be generally from left to right, or in the direction of the process. The "cross-machine direction" is generally perpendicular to, or across the machine direction. Referring to FIG. 3, the puck assembly 38 initially is oriented lengthwise parallel to the machine direction, and as shown in FIG. 4, rotates roughly 90° so that the puck assembly 38 is oriented lengthwise in the cross-machine direction. Referring to FIGS. 3 and 4 vacuum slides 34 will exhibit linear movement along the arrows shown in FIG. 4, with directional components of the linear movement in both the machine direction (left to right relative to the orientation of FIG. 3) and the cross-machine direction (up and down relative to the orientation of FIG. 3).

As shown in FIG. 3, a top view of an embodiment of an active pad turning puck 16 of the present invention is shown. A plurality of vacuum slides 34 are positioned about a puck assembly 38. The vacuum slides 34 are intended to engage a portion of articles 14 (not shown) by vacuum ports 42, and manipulate by stretching or otherwise the articles 14. As is well known in the art, each of the segments can be connected internally to a source of vacuum. A pattern of holes is provided on the surface of each segment through which the internal vacuum acts to draw the pads 14 towards the surface. It is clear that this technology can be applied to the transfer and placement of many different types of articles in the disposable goods industry and other industries as well.

In use, rotation of the puck assembly 38 relative to a cam plate 40 causes cam followers 32 to track through channels 36. Channels 36 are of an increasing radius from the center of the cam plate 40. Because cam followers 32 are coupled with vacuum slides 34, rotation of the puck assembly 38 relative to the cam plate 40 causes sliding of the vacuum slides inwardly and outwardly as shown in FIG. 4. The cam followers 32 are urged inwardly and outwardly due to the increasing radius of the channels 36 in a first direction of travel, and the decreasing radius of channels 36 in the second rotational direction of travel, preferably in a washing machine-like back and forth style.

Figure 5:
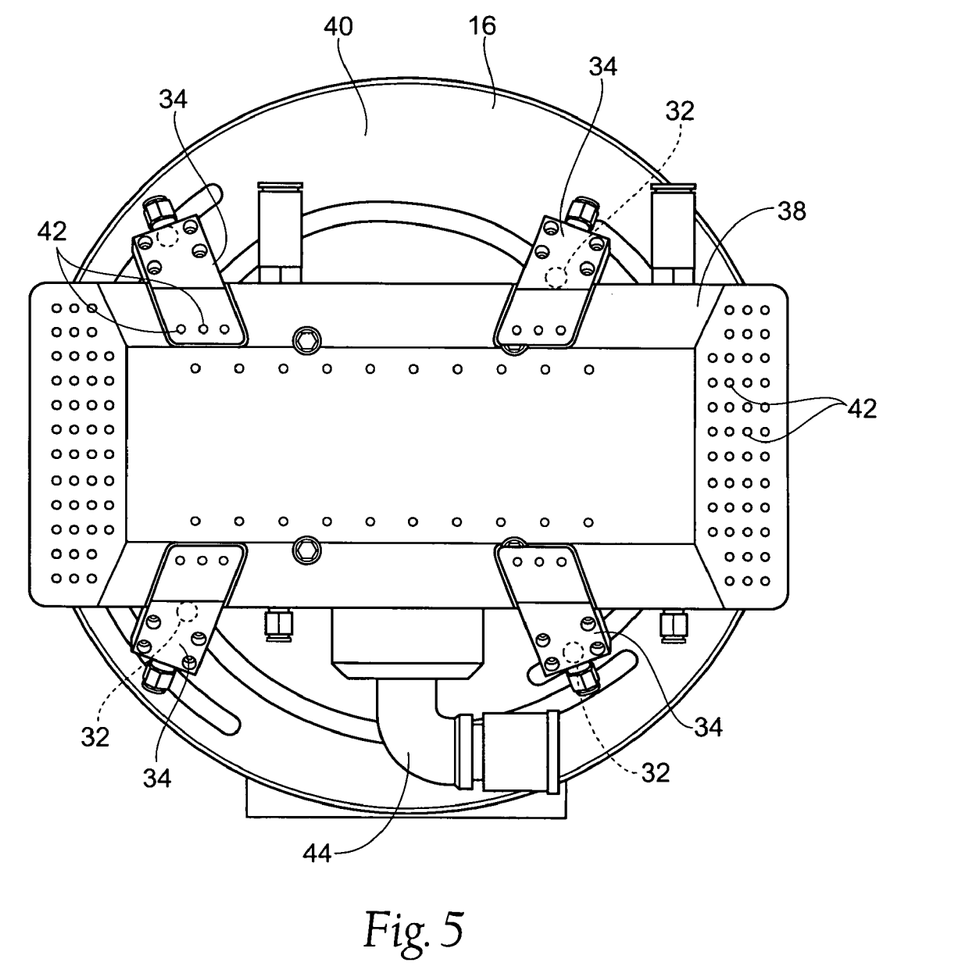
FIG. 5 is a top view of-an embodiment of an active pad turning puck of the present invention.

Referring now to FIG. 5, a top view the active pad turning puck 16 of the present invention is shown. In this embodiment, vacuum ports 42 are shown, and may be applied to the vacuum slides 34, the puck assembly 38, or both. The vacuum ports are coupled to a manifold 44 and ultimately a source of vacuum (not shown).

Figure 6:
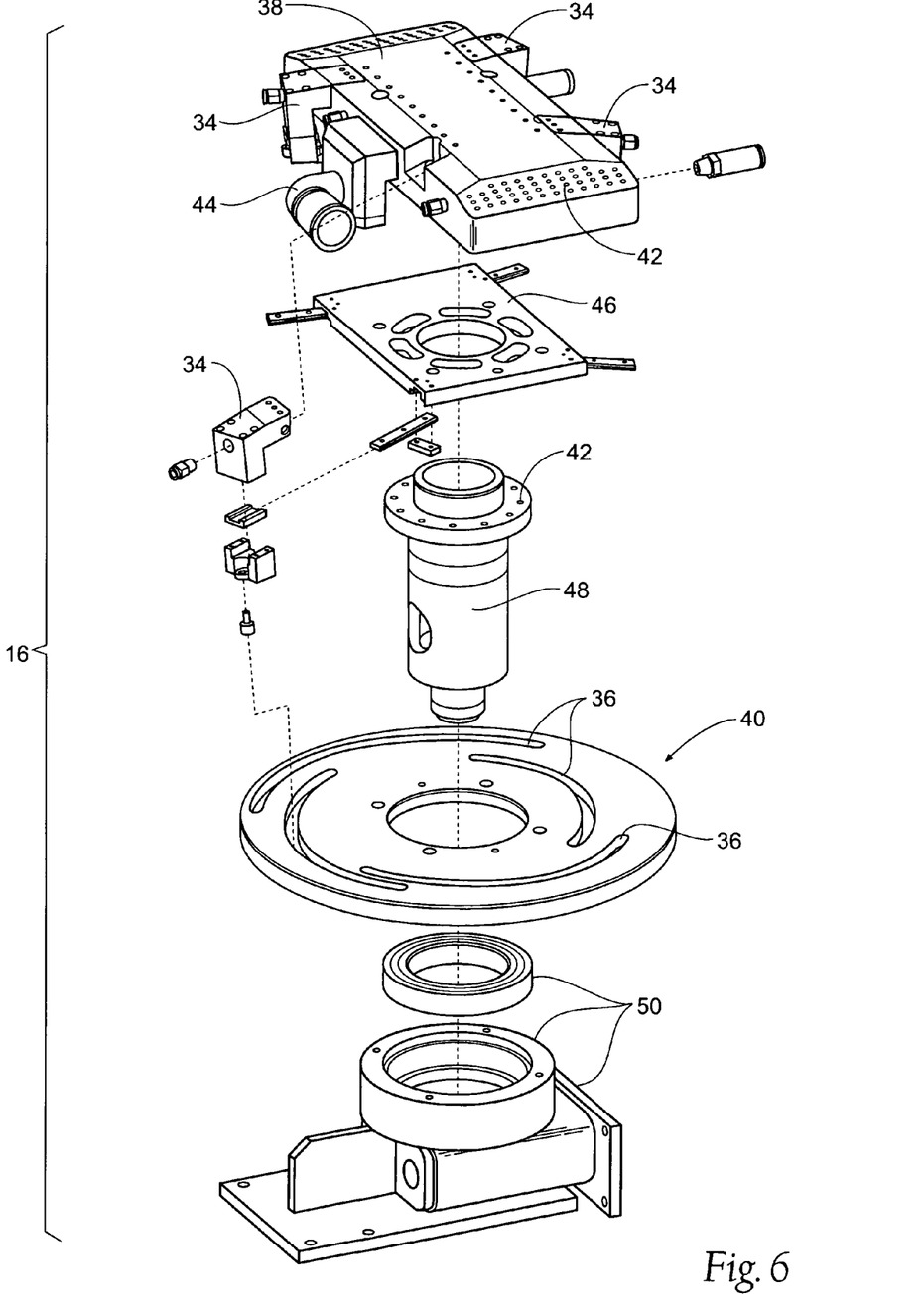
FIG. 6 is an exploded view of an active pad turning puck of the present invention.

Referring now to FIG. 6, an exploded view of the active pad turning puck 16 of the present invention is shown. In this embodiment, a shaft adaptor plate 46 is shown to receive shaft 48, through a void provided proximal to the center of cam plate 40. The support subassembly 50 is provided for coupling of the puck 16 to the pad turning device 12.

Figure 7:
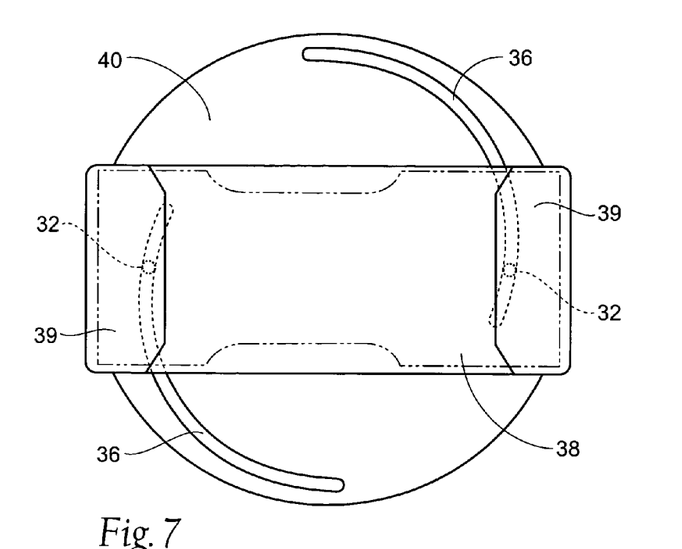
FIG. 7 is a top view of an alternate embodiment of an active pad turning puck of the present invention.
Figure 8:
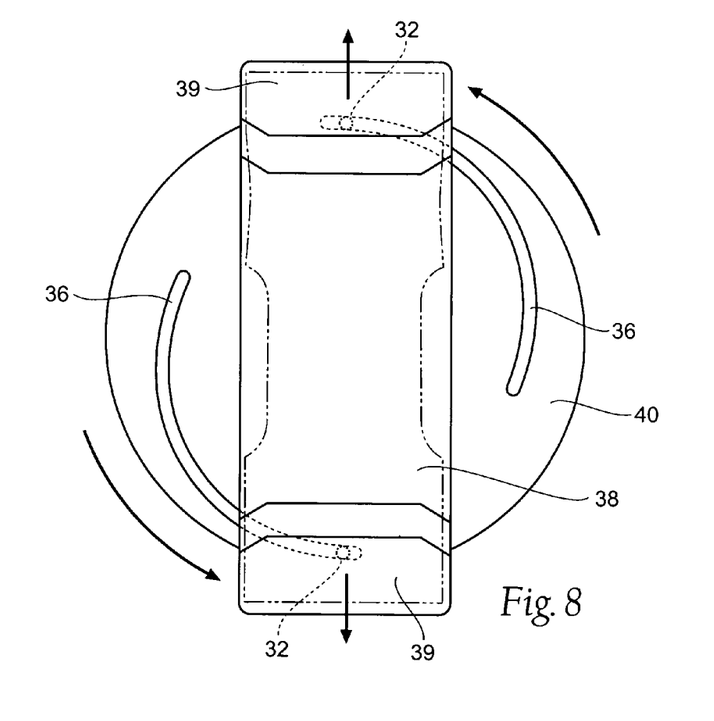
FIG. 8 is a top view of an alternate embodiment of an active pad turning puck of the present invention.

Referring now to FIG. 7, a top view of an alternate embodiment of an active pad turning puck 16 of the present invention is shown. In this embodiment, ends 39 of the puck assembly 38 are slidably enabled, as the vacuum slides 34 described previously. Rotation is again a driving force of sliding movement caused by the cam follower 32 coupled to the ends 39, as shown in FIG. 8.

Figure 9:
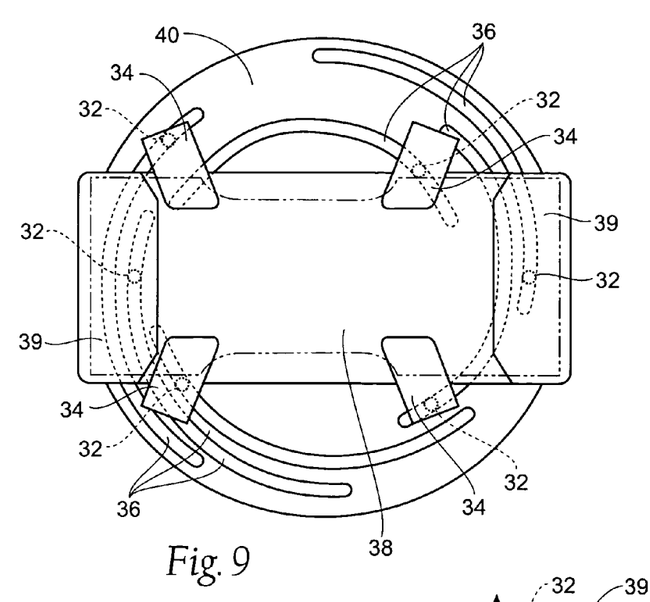
FIG. 9 is a top view of an additional alternate embodiment of an active pad turning puck of the present invention.
Figure 10:
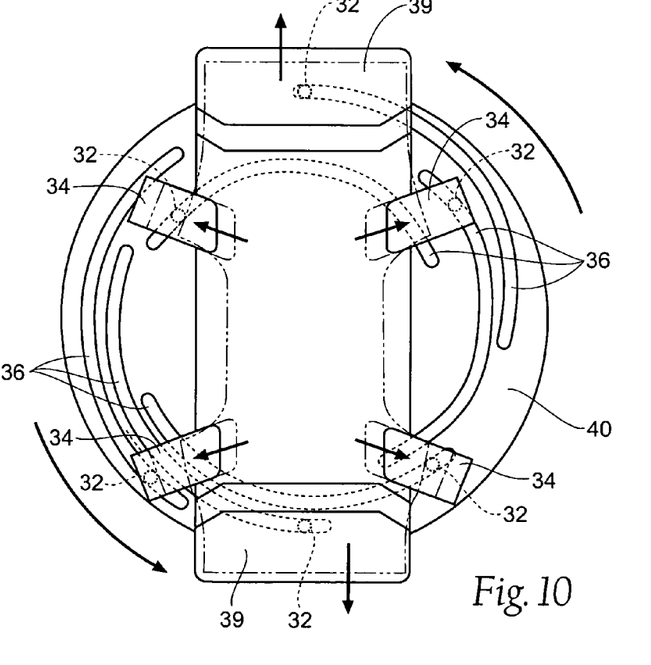
FIG. 10 is a top view of an additional alternate embodiment of an active pad turning puck of the present invention.

Referring now to FIGS. 9 and 10, a top view of an additional alternate embodiment of an active pad turning puck 16 of the present invention is shown. In this embodiment, a plurality of channels 36 are provided, each channel 36 receiving a cam follower 32 coupled to a slidable element, either ends 39 or slides 34. Of course, a single circuitous channel 36 could be provided for receiving multiple cam followers 32. Again, cam followers 32, upon rotation, urge the slidable elements outward and inward.

Figure 11:
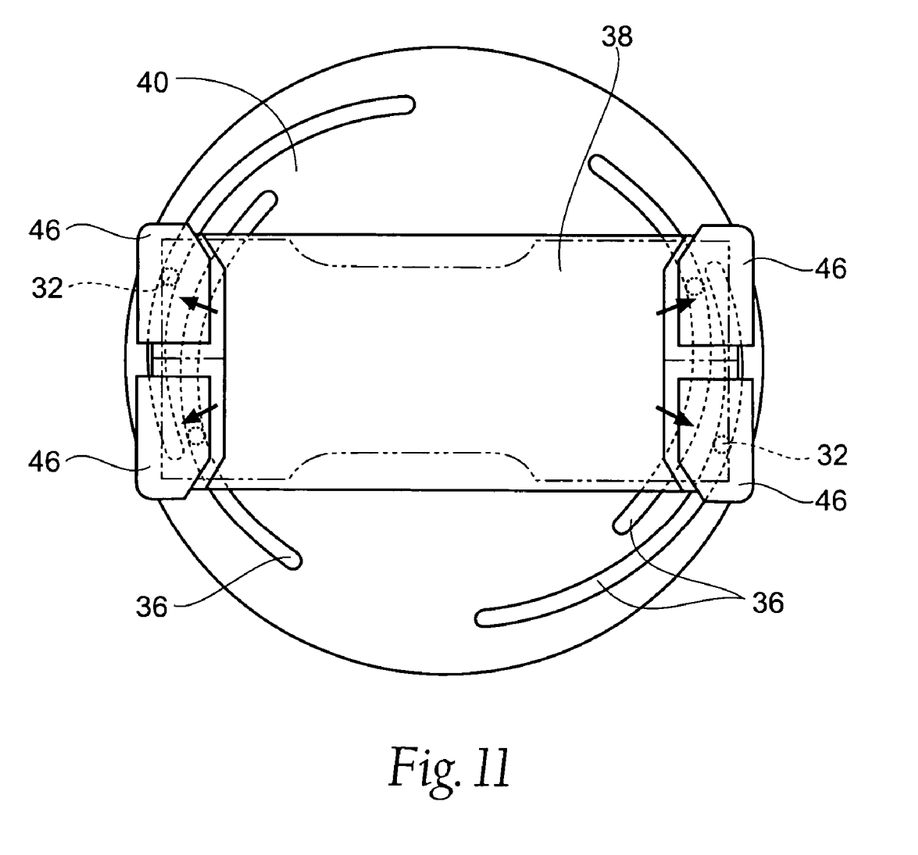
FIG. 11 is a top view of an additional alternate embodiment of an active pad turning puck of the present invention.

Referring now to FIG. 11, an additional alternative embodiment of a puck 16 of the present invention is shown. In this embodiment, it can be seen that a slidable elements 46 are provided at corners of the puck assembly 38. These slidable elements 46 will move somewhat radially away from the center of the puck 16, although the direction of movement can be controlled through different arrangements of the channel or channels 36.

In use, the transfer apparatus 10 rotates from the pick up point, stretches the article 14 while the article is upon a puck 16 by slidable elements, and deposits the article 14 on a conveyor 28 or the like for downstream processing. As the puck 16 rotates between the pick up and deposition points, the cam followers are urged into an increasing radius of the channel 36. Between the deposition point and the next subsequent pick up point, the puck 16 will rotate back to its initial position, and the cam followers are urged into an its decreasing radius of the channel 36, causing the slidable elements 34 or 39 to return to their initial, retracted position, ready to receive another article 14.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. An apparatus for transferring articles from a first conveying device onto a second conveying device comprising:
   an article traveling in a machine direction,
   a cam plate comprising a guiding structure of variable radius;
   a plurality of vacuum slides configured to cooperate with said guiding structure of variable radius,
   a vacuum puck carrying said article, said puck coupled with said vacuum slides,
   wherein said vacuum slides in response to rotation of said vacuum puck relative to said cam plate,
   and wherein said vacuum puck rotates said article in a cross-machine direction, and wherein said vacuum slides urge manipulation of said article in directions having a cross-machine and a machine direction component during said rotation.

2. An apparatus for transferring articles from a first conveying device onto a second conveying device comprising:
   a cam plate comprising a guiding structure of variable radius;
   a first vacuum slide configured to cooperate with said guiding structure of variable radius,
   a second vacuum slide configured to cooperate with said guiding structure of variable radius,
   a third vacuum slide configured to cooperate with said guiding structure of variable radius,
   a vacuum puck carrying said article, said puck coupled with said vacuum slides,
   said vacuum slides sliding in response to rotation of said vacuum puck relative to said cam plate,
   said first vacuum slide sliding in a first slide orientation relative to a machine direction, and
   said second vacuum slide sliding in a second slide orientation relative to the machine direction;
   said third vacuum slide sliding in a third slide orientation relative to the machine direction;
   thereby stretching said article in directions parallel and skew to the machine direction.

3. An apparatus for transferring articles from a first conveying device onto a second conveying device comprising:
- an article traveling in a machine direction,
- a cam plate comprising a guiding structure of variable radius;
- a plurality of vacuum slides configured to cooperate with said guiding structure of variable radius,
- a vacuum puck carrying said article, said puck coupled with said vacuum slide,
- wherein said vacuum slides sliding in response to rotation of said vacuum puck relative to said cam plate,
- and wherein said vacuum puck rotates said article relative to the machine direction to a cross-machine direction, and wherein said vacuum slides urge manipulation of said article in more than one direction during said rotation;
- said vacuum puck comprising a first stretching target zone and a second non-stretching target zone.

* * * * *